United States Patent [19]

Maydan et al.

[11] 4,227,088
[45] Oct. 7, 1980

[54] HIGH SPEED COMPUTER ASSISTED TOMOGRAPHY

[75] Inventors: Dan Maydan, Short Hills; Lawrence A. Shepp, South Plainfield, both of N.J.

[73] Assignee: Bell Telephone Laboratories, Incorporated, Murray Hill, N.J.

[21] Appl. No.: 949,979

[22] Filed: Oct. 10, 1978

[51] Int. Cl.³ .................. G01N 21/34; G01N 23/04
[52] U.S. Cl. .......................... 250/445 T; 250/360
[58] Field of Search ............. 250/445 T, 360; 313/60

[56] References Cited

U.S. PATENT DOCUMENTS

| | | | |
|---|---|---|---|
| 3,940,625 | 2/1976 | Hornsfield | 250/360 |
| 4,128,781 | 12/1978 | Flisikowski | 313/60 |
| 4,135,095 | 1/1979 | Watanabe | 250/445 T |
| 4,137,455 | 1/1979 | Fetter | 250/445 T |
| 4,153,842 | 5/1979 | Rohmfeld | 250/445 T |

OTHER PUBLICATIONS

Iinuma, Tateno, Umegaki, and Watanage, "Proposed System for Ultrafast Computed Tomography", *Journal of Computer Assisted Tomography*, 1/4/77, pp. 494-498.

Primary Examiner—Alfred E. Smith
Assistant Examiner—Thomas P. O'Hare
Attorney, Agent, or Firm—Stephen J. Phillips; Jack S. Cubert

[57] ABSTRACT

X-ray generation and detection apparatus for use in a computer assisted tomography system which permits relatively high speed scanning. A large X-ray tube having a circular anode (3) surrounds the patient area. A movable electron gun (8) orbits adjacent to the anode. The anode directs into the patient area X-rays which are delimited into a fan beam by a pair of collimating rings (21). After passing through the patient, X-rays are detected by an array (22) of movable detectors. Detector subarrays (23) are synchronously movable out of the X-ray plane to permit the passage of the fan beam.

5 Claims, 1 Drawing Figure

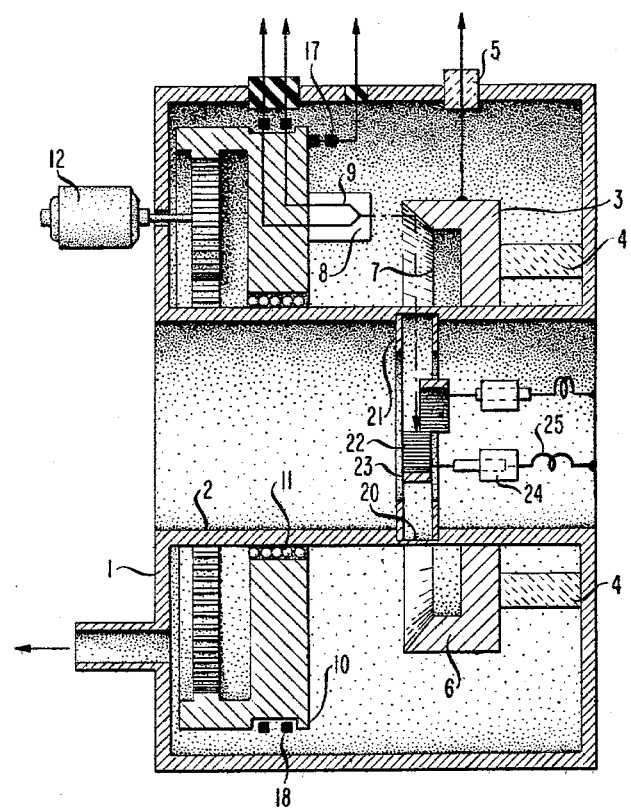

HIGH SPEED COMPUTER ASSISTED TOMOGRAPHY

TECHNICAL FIELD

This invention relates to transaxial X-ray tomography systems, and more particularly, to high-speed computer assisted tomography.

BACKGROUND OF THE INVENTION

In medical applications of computer assisted tomography (CAT) it is desirable to achieve scan time of about 0.1 sec in order to image portions of the body during live motion such as heartbeat or respiration. The usual source of X-rays in conventional CAT systems is the Coolidge tube. The entire X-ray tube is translated or orbited or both as necessary to provide X-ray projections for planar image reconstruction. One such design using a conventional X-ray tube mechanically orbited about the patient area on a gantry is set forth in U.S. Pat. No. 3,940,625 by Hounsfield issued Feb. 24, 1976.

The Coolidge X-ray tube has relatively high mass and is not designed to withstand the strong accelerating forces necessary for rapid movement and fast scanning. Use of the conventional X-ray tube limits scan time to a few seconds, too slow for live stop-action images.

An ultrafast CAT scanner has been proposed which is intended to reduce scan time to 0.01 sec. (See "Proposed System for Ultrafast Computed Tomography," by Iinuma, Tateno, Umegaki, and Watanabe, in *Journal of Computer Assisted Tomography*, Vol. 1, No. 4, 1977, pp. 494-498.) The ultrafast system uses a large bell-shaped X-ray tube containing a circular conic anode surrounding the patient area. A system of deflection coils directs an axial electron beam to the anode and around the anode circle for X-ray generation. The X-rays are directed through the patient area to a circular array of stationary detectors axially displaced from the plane of the X-ray beam. Focusing of the electron beam over the relatively long beam path is difficult and contributes to the complexity and expense of the ultrafast system. Further, the detector array, being out of the X-ray beam plane, gives X-ray projection data for a conic surface and not for a true transaxial plane through the patient area. This produces images of lower resolution than true planar measurements would produce.

SUMMARY OF THE INVENTION

The present invention provides for fast CAT scanning with speeds suitable for imaging a beating heart or respiratory motion but without the complexity of a long electron beam path for X-ray generation. Further, the present invention provides for true planar measurements of X-ray projections.

The present invention achieves these goals by providing an open cylindrical X-ray tube containing a circular conic anode surrounding the patient area, with an electron source movable in a circular orbit adjacent to the anode. Since the mass of the electron source is considerably less than the mass of an entire Coolidge X-ray tube, the source can be orbited at a relatively high speed. Detectors are arranged in a circular array in the X-ray beam plane. Detectors are movable out of the path of the X-ray beam to prevent the incoming X-ray beam from illuminating the detector rear surface and thus shadowing the patient area. Detector movement is synchronized with the motion of the electron source so that detectors on the opposite side of the patient area are in the X-ray plane at the proper time for X-ray detection.

BRIEF DESCRIPTION OF THE DRAWING

The FIGURE shows a computer assisted tomography system constructed according to the present invention.

DETAILED DESCRIPTION

The FIGURE shows a cut away side view of an X-ray generation and detection arrangement constructed according to the present invention. Detected X-ray signals are processed by digital computer to reconstruct an image of a transaxial slice through the patient area in the conventional way. These matters will not be further discussed.

X-ray generation takes place in a donut-shaped vacuum chamber 1. Vacuum supporting inner walls 2 surround the patient area in cylindrical fashion. Circular anode 3 is supported within the vacuum chamber by high voltage insulators 4. Feedthrough insulator 5 carries current through the wall of the vacuum chamber to maintain a suitably high voltage at anode 3 for X-ray generation. The outer periphery of the anode 3 projects in an axial direction forming a cylindrical projection 6 of the anode. Cylindrical projection 6 terminates in conic anode surface 7 coated with a suitable X-ray generating material such as tungsten.

Electron gun 8 includes a hot filament electron emitter 9 positioned adjacent to anode surface 7. Current is applied to emitter 9 through brush and contact arrangement 18. Rings of conducting material extend around the circumference of rotational structure 10 with sliding brush contacts for conducting filament current through the vacuum supporting wall from a suitable power supply. Heating current supplied to the filament of emitter 9 supports thermionic emission of electrons which are accelerated to strike anode surface 7 causing X-ray emission.

Electron gun 8 is attached to rotational structure 10 supported by bearings 11. Structure 10 is in the form of an annular circular ring rotatable concentrically with anode 3. As structure 10 rotates, the axial and radial relationship between electron gun 8 and anode surface 7 remains constant, thereby providing a relatively constant intensity of X-rays emitted from each point of anode surface 7 as the electron gun passes. Rotational motion of structure 10 is imparted by motor, shaft, and gear arrangement 12, which extends through the vacuum supporting wall with a vacuum supporting seal.

X-rays produced at anode surface 7 pass through an X-ray transparent window 20 of the vacuum supporting wall. This X-ray window may be of any suitable mechanically rigid material such as beryllium. X-rays emerging from anode surface 7 are collimated into a fanshaped beam by circular annular delimiters 21 made of a suitable X-ray opaque material such as lead.

The X-ray beam impinges upon X-ray detector array 22. The output of array 22 is conveyed to the input of an image reconstruction computer, not shown. Detectors in array 22 form a complete circle around the patient area in the plane of the X-ray fan beam. Detectors are axially movable, either individually or in convenient mechanically connected detector subarrays such as subarray 23, each subarray comprising a suitable fraction of the total array circle. For illustrative purposes, subarray 23 comprises one-fourth of the detectors. Each subarray is movable in the axial direction by a suitable withdrawing element such as solenoid 24. When energized, the solenoid moves subarray 23 out of the path of the X-ray fan beam, thus allowing the fan beam to pass through the patient area and illuminate detectors positioned on the opposing side. Subarray 23 is restored to its position in the beam plane by the action of a suitable restoring element such as compression spring 25.

A subarray may comprise any number of one or more detectors. In some applications it may be necessary to move or restore more than one subarray at a time to allow the fan beam to pass unobstructed and to assure that detectors are timely returned to the beam plane.

In operation, motion of the detector subarrays is synchronized with the rotation of structure 10. To this end, suitable position detector 17 is associated with rotational structure 10. Detector 17 may be of mechanical, electrical, optical or other conventional design for determining the rotational position of structure 10.

We claim:

1. Apparatus for X-ray generation and detection for use in a transverse section computer assisted tomography system comprising a fixed circular anode (3) surrounding a patient area, a source (8) of electrons impinging upon said anode thereby producing X-rays directed through the patient area, and a circular array of detectors (22) characterized in that said source of electrons is a single electron producing structure incorporated on a rotatable ring adjacent to said fixed circular anode, said ring surrounds the patient area and is substantially concentric with the longitudinal axis of the patient area; said single electron producing structure being orbitally movable by said ring around the patient area adjacent to said fixed circular anode, and said detectors lie in the X-ray beam plane and are partitioned into groups, each group being movable out of said plane synchronously with the movement of said single electron producing structure.

2. Apparatus as set forth in claim 1 further comprising means (17) for detecting the orbital position of said electron producing structure and means (24,25) for moving said detectors.

3. Apparatus as set forth in claim 1 wherein said detectors are movable axially with relation to said anode.

4. Apparatus as set forth in claims 1, 2, or 3 wherein said electron producing structure includes an electron gun.

5. Apparatus as set forth in claims 1, 2, or 3 wherein said electron producing structure includes a hot filament electron emitter.

* * * * *